US010406161B2

(12) United States Patent
Sun et al.

(10) Patent No.: US 10,406,161 B2
(45) Date of Patent: *Sep. 10, 2019

(54) RISPERIDONE SUSTAINED RELEASE MICROSPHERE COMPOSITION

(71) Applicants: Shandong Luye Pharmaceutical Co., Ltd., Yantai, Shandong (CN); Nanjing Luye Pharmaceutical Co., Ltd., Nanjing, Jiangsu Province (CN)

(72) Inventors: Kaoxiang Sun, Yantai (CN); Rongcai Liang, Yantai (CN); Qilin Wang, Yantai (CN); Wenyan Wang, Yantai (CN); Wanhui Liu, Yantai (CN); Youxin Li, Yantai (CN)

(73) Assignees: SHANDONG LUYE PHARMACEUTICAL CO., LTD., Yantai (CN); NANJING LUYE PHARMACEUTICAL CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,614

(22) Filed: Sep. 27, 2018

(65) Prior Publication Data

US 2019/0022098 A1    Jan. 24, 2019

Related U.S. Application Data

(63) Continuation of application No. 15/347,365, filed on Nov. 9, 2016, now Pat. No. 10,098,882, which is a continuation of application No. 15/217,696, filed on Jul. 22, 2016, now Pat. No. 9,532,991, which is a continuation of application No. 14/113,738, filed as application No. PCT/CN2012/000473 on Apr. 10, 2012, now Pat. No. 9,446,135.

(30) Foreign Application Priority Data

Apr. 25, 2011    (CN) .......................... 2011 1 0102840

(51) Int. Cl.
| | |
|---|---|
| *A61K 9/50* | (2006.01) |
| *A61K 31/519* | (2006.01) |
| *A61K 9/16* | (2006.01) |
| *A61K 9/19* | (2006.01) |
| *A61K 9/14* | (2006.01) |
| *A61K 47/34* | (2017.01) |
| *A61K 9/00* | (2006.01) |
| *A61K 9/48* | (2006.01) |

(52) U.S. Cl.
CPC .......... *A61K 31/519* (2013.01); *A61K 9/0019* (2013.01); *A61K 9/14* (2013.01); *A61K 9/1647* (2013.01); *A61K 9/19* (2013.01); *A61K 9/4858* (2013.01); *A61K 9/5031* (2013.01); *A61K 9/5089* (2013.01); *A61K 47/34* (2013.01); *A61K 9/16* (2013.01)

(58) Field of Classification Search
None
See application file for complete search history.

(56) References Cited

U.S. PATENT DOCUMENTS

| 5,871,778 | A  | 2/1999  | Kino et al. |
| 2004/0266791 | A1 | 12/2004 | Gieling et al. |
| 2006/0110434 | A1 | 5/2006  | Yamaguchi et al. |
| 2009/0004283 | A1 | 1/2009  | Peterson et al. |

FOREIGN PATENT DOCUMENTS

| CN | 1137756 A    | 12/1996 |
| CN | 101292960 A  | 10/2008 |
| CN | 101584652 A  | 11/2009 |
| CN | 101653422 A  | 2/2010  |
| CN | 103338752 B  | 10/2014 |
| JP | 2004-532218 A | 10/2004 |
| JP | 2009-520727 A | 5/2009  |
| JP | 2009-155302 A | 7/2009  |
| JP | 2010-531807 A | 9/2010  |
| WO | 2008/153611 A2 | 12/2008 |
| WO | 2012/019009 A1 | 2/2012  |

OTHER PUBLICATIONS

Anderson et al., "Biodegradation and biocompatibility of PLA and PLGA microspheres," *Advanced Drug Delivery Reviews* 28:5-24, 1997.
Canadian Examination Report for Application No. 2,832,663 dated Jun. 10, 2015.
Canadian Office Action for Application No. 2,832,663 dated Jan. 12, 2015.
Chinese Office Action for Application No. 201280006994.7 dated Mar. 13, 2014.
Chinese Office Action for Application No. 201410314847.7 dated Jan. 5, 2016.
Chinese Office Action for Application No. 201410314847.7 dated Sep. 13, 2016.

(Continued)

*Primary Examiner* — James W Rogers
(74) *Attorney, Agent, or Firm* — Seed IP Law Group LLP

(57) ABSTRACT

A risperidone sustained release microsphere formulation is provided. The microsphere formulation comprise risperidone or 9-hydroxy risperidone or salts thereof, and a polymer blend having a first uncapped lactide-glycolide copolymer and a second uncapped lactide-glycolide copolymer, in which the first uncapped lactide-glycolide copolymer is a copolymer with a high intrinsic viscosity and the second uncapped lactide-glycolide copolymer is a copolymer with a low intrinsic viscosity. The sustained release microsphere formulation according to an embodiment of the present disclosure is suitable for large-scale industrialized production with improved stability, the in vivo release behavior of which will not change after long-term storage.

20 Claims, 3 Drawing Sheets

(56) References Cited

OTHER PUBLICATIONS

European Examination Report for Application No. 12777430.5 dated Sep. 30, 2015.
European Office Action for Application No. 12777430.5 dated Mar. 1, 2016, 6 pages.
European Office Action, dated Jan. 11, 2018, for European Application No. 16 179 390.6-1109, 6 pages.
Extended European Search Report, dated Jun. 29, 2017, for European Application No. 16179390.6-1455, 8 pages.
First Australian Examination Report for Application No. 2012248038 dated Apr. 13, 2015.
Fude (ed.), *Pharmaceutics*, 5$^{th}$ ed., The People's Medical Publishing House, Beijing, China, 2004, pp. 58, 84-85. (with English Translation) (10 pages).
Graves et al. "Effect of different ratios of high and low molecular weight PLGA blend on the characteristics of pentamidine microcapsules," *International Journal of Pharmaceutics* 270:251-262, 2004.
Guoguang et al., "Study on sustained-release risperidone biodegradable microspheres," *Journal of China Pharmaceutical University* 37(6):512-515, 2006. (English translation of Abstract provided herewith).
International Search Report and Written Opinion application No. PCT/CN2012/000473 dated Jul. 19, 2012, 9 pages.
Japanese Office Action for Application No. JP2014-506723 dated Nov. 18, 2014.
Lane et al., "Risperidone in Acutely Exacerbated Schizophrenia: Dosing Strategies and Plasma levels," *J. Clin Psychiatry* 61(3):209-214, 2000.
Lei, "Studies on preparation and release in vitro of risperidone loaded long-acting injectable microspheres," *China Pharmacist* 12(12):1713-1715, 2009.
Lewis, "Controlled Release of Bioactive Agents from Lactide/Glycolide Polymers," in Mark Chasin et al. (eds.), *Biodegradable Polymers as Drug Delivery Systems*, Marcel Dekker, Inc., New York, 1990, pp. 1-41. (52 pages).

Notice of Opposition to a European Patent, dated Jun. 20, 2017, regarding European Patent No. 2701687, 15 pages.
Office Action No. 1 Issued in Japan; Application No. 2015-075711; dated Jan. 26, 2016, 6 pages.
Office Action No. 2 Issued in Japan; Application No. 2015-075711; dated Jul. 26, 2016, 8 pages.
Pajonk, "Risperidone in acute and long-term therapy of Schizophrenia—a clinical profile," *Progress in Neuro-Psychopharmacology & Biological Psychiatry* 28: 15-23, 2004.
Qinghua et al., "Clinical Advantages of an injectable long-acting risperidone microspheres," *Chinese Pharmacy*, 15(15): 1235-1238, 2006. (English Translation of abstract provided herewith).
Ravivarapu et al., "Polymer and microsphere blending to alter the release of a peptide from PLGA microspheres," *European Journal of Pharmaceutics and Biopharmaceutics* 50:263-270, 2000.
Renken, Written submissions pursuant to Rule 116 EPC, dated Jul. 24, 2018, for European Patent No. 2 701 687 B1, 5 pages.
Response to European Office Action for Application No. 12777430.5 dated Mar. 1, 2016, 6 pages. Response filed Apr. 14, 2016, 20 pages.
Second Australian Examination Report for Application No. 2012248038 dated Jul. 20, 2015.
Summons to attend oral proceedings pursuant to Rule 115(1) EPC, dated Mar. 7, 2018, for European Application No. 12777430.5-1109, 11 pages.
Supplementary European Search Report for application No. EP 127777 430 dated Oct. 13, 2014.
Zheng-Xing Su et al., "Biodegradable poly(D, L-lactide-co-glycolide) (PLGA) microspheres for Sustained release of risperidone: Zero-order release formulation," *Pharmaceutical Development and Technology*, 16(4): 377-384, 2011.
Zhengxing Su et al., "Effects of Formulation Parameters on Encapsulation Efficeicy and Release Behavior of Risperidone Poly (D,L-lactide-co-glycolide) Microsphere," *Chem. Pharm. Bull* 57(11):1251-1256, 2009.
Decision rejecting the opposition (Art. 101(2) EPC), dated Oct. 31, 2018, for European Patent No. 2 701 687 B1, 35 pages.
Submission in Opposition Proceedings, dated Mar. 8, 2019, for European Application No. 12777430.5, 22 pages.

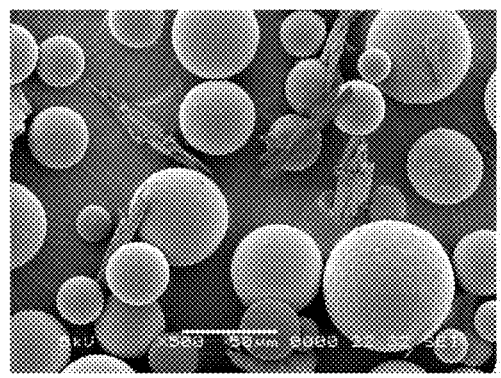 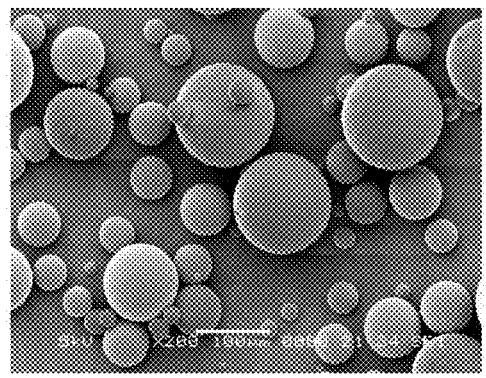
Fig.1-1    Fig.1-2
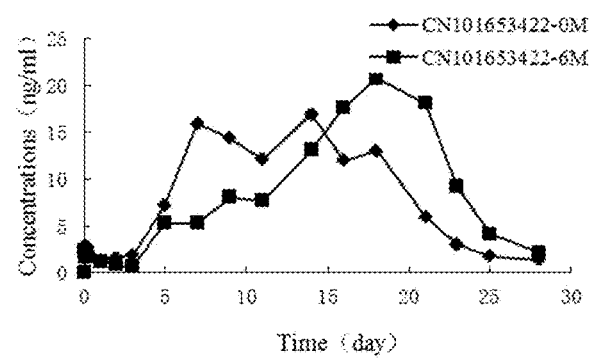
Fig.2
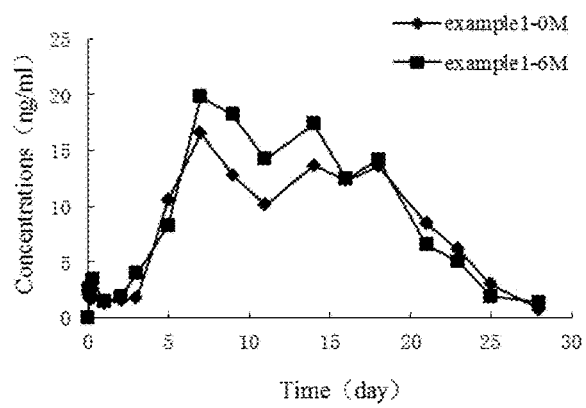
Fig.3

RISPERIDONE SUSTAINED RELEASE MICROSPHERE COMPOSITION

CROSS-REFERENCE TO RELATED APPLICATIONS

This application is a continuation application of U.S. application Ser. No. 15/347,365 filed on Nov. 9, 2016 (now allowed) which is a continuation of U.S. application Ser. No. 15/217,696 filed Jul. 22, 2016 (now issued as U.S. Pat. No. 9,532,991 on Jan. 3, 2017) which is a continuation of Ser. No. 14/113,738 filed Oct. 24, 2013 (now issued as U.S. Pat. No. 9,446,135 on Sep. 20, 2016) and which is a 371 of International Application No. PCT/CN2012/000473 filed on Apr. 10, 2012 (now expired) and claims priority to CN Application No. 201110102840.5 filed on Apr. 25, 2011, which applications are incorporated herein by reference in their entireties.

FIELD

The present disclosure belongs to pharmaceutical preparation field, and more particularly relates to a risperidone long-acting sustained release microsphere composition, method for preparing the same and use of the same.

BACKGROUND

Schizophrenia is a serious disabling mental disorder. With the development of intense social competition, quick pace of life and changes in family structure, people face greater pressure than before, and consequently mental health problems become more and more prevalent. Schizophrenia is the most common disease in mental disorder. According to statistics, the prevalence of schizophrenia in China is 6.55%0, there are more than 7.8 million schizophrenes, and the global disease rate is as high as 1.5%.

Antipsychotic drugs, also referred to as neuroleptic, may control mental symptoms of schizophrenia effectively. The commonly used antipsychotic drugs first appeared in 1950s, such as chlorpromazine or haloperidol, have a main pharmacological effect of blocking central dopamine $D_2$ receptor and are effective in the treatment of positive psychosis symptoms, but may cause extrapyramidal movement disorders, and are invalid for negative symptoms and cognitive function damage, accompanying with many adverse reactions, also have greater toxicity on cardiovascular and liver with larger administration dose, and significant side effects. In order to overcome these shortcomings, since 1980s, new antipsychotic drugs appeared, main pharmacological effect of which is to block $5-HT_{2A}$ and $D_2$ receptors. The advantages of new antipsychotic drugs are that not only in the treatment of acute exacerbation of psychiatric patients, but also in the treatment of extrapyramidal symptoms and tardive dyskinesia, which have little side effects without the use of anticholinergic agents; tolerance and compliance of the treatment are good; therapeutic effects in improving positive and negative symptoms and cognitive function are strong, adverse reactions of extrapyramidal system (EPS) may be less or may not be caused, and endocrine adverse reactions may not be caused by the increase of prolactin levels.

Risperidone as a representative of new antipsychotic drugs was developed by Janssen Pharmaceutica in Belgium in 1984, with the chemical name of 3-[2-[4-(6-fluoro-1,2-benzisoxazole-3-yl)-1-piperidyl]ethyl]-6,7,8,9-tetrahydro-2-methyl-4H-pyrido[1,2-c]pyrimidine-4-one, has a good therapeutic effect on positive symptoms and negative symptoms of schizophrenia, and the incidence rate of extrapyramidal adverse reactions is low. A metabolite of risperidone, i.e., 9-hydroxy risperidone (paliperidone) has pharmacological effects similar to those of risperidone. Risperidone and 9-hydroxy risperidone together constitute the active ingredients of antipsychotic drugs.

Commonly used clinical dosage forms of risperidone comprise tablets, oral solutions, capsules, and orally disintegrating tablets, etc. For common dosage forms of risperidone, drugs usually have to be taken every day, which is difficult for about 75% of psychiatric patients. This is also a very important factor contributing to deterioration during the treatment.

In order to solve such problems, researchers have actively developed risperidone long-acting sustained release preparations. For example, CN1137756, the entire content of which is incorporated herein by reference, disclosed a risperidone sustained release microsphere composition prepared by using a polymer matrix material with a molecular weight of 100,000 to 300,000. Long-acting antipsychotic drug Risperidal Consta (Chinese name: HENGDE), which developed based on the technology in CN1137756, came into market in August 2002. The product is prepared by encapsulating risperidone in a lactide-glycolide copolymer (PLGA) with a molecular weight of 150,000, suspended in a solution, and administered by intramuscular injection once every 2 weeks, thus avoiding the peak-valley concentration of daily administration effectively. However, only a small amount of drug in the preparation is released on the first day, followed by a drug release lag phase after 3 weeks, and with the degradation of the microsphere skeleton, most of drugs are released in the 4th to 6th weeks [Chen Qinghua, Chen Gang, et al, pharmacokinetic characteristics and clinical application of risperidone long-acting injection, Chinese Pharmacy, 2006, 15 (15):1235-1238]. Therefore, while the drug is administrated to patients by injection in the first 3 weeks, patients also need to rely on oral risperidone tablets to achieve therapeutic effects, and subsequently the clinical use is not convenient and patient compliance is poor.

Chen Guoguang et al reported a risperidone microsphere composition prepared by using PLGA (50:50, molecular weight of 30,000) with a drug-loading rate of 18%, by which a stable drug blood concentration may be maintained in vivo for 5-20 days [Chen Guoguang, Tang Jun, et al, study on risperidone biodegradable microspheres, Journal of China Pharmaceutical University, 2006, 37 (6):512-515]. However, the drug-loading rate of this microsphere composition is low, and is also accompanied with a burst release when the drug-loading rate is low.

CN101653422, the entire content of which is incorporated herein by reference, disclosed a risperidone microsphere composition which may cause sustained release for more than 4 weeks, and the drug release lag phase was eliminated by improving the drug-loading rate (above 45%), substantially solve burst release problems. However, the patent application of CN101653422 only verifies that the laboratory level (5 L scale) may achieve the desired object. It has been found by the applicant of the present invention that drug crystals were precipitated out during the scaled-up production of risperidone microspheres provided in CN101653422, the preparation stability was poor, and in vivo release behavior of the microspheres will change substantially after long-term storage.

As is well known, large-scale industrialized production has always been the bottleneck of the industrialization of the microsphere preparation, and therefore there is an urgent need to provide a formulation of risperidone microspheres that is stable in quality and suitable for large-scale industrialized production.

SUMMARY

The present disclosure provides a pharmaceutical microsphere composition, containing an active ingredient and an uncapped poly(lactide-co-glycolide), in which the active ingredient is selected from risperidone or a salt thereof, and 9-hydroxy risperidone or a salt thereof; the uncapped poly (lactide-co-glycolide) consists of two copolymers; a weight content of the active ingredient in the pharmaceutical composition is within a range from 10% to 60%, preferably, from 35% to 55%, more preferably, from 40% to 50%; and a weight content of the uncapped poly(lactide-co-glycolide) in the pharmaceutical composition is within a range from 40% to 90%, preferably, from 45% to 65%, more preferably, from 50% to 60%.

The microspheres as disclosed herein is: Small spherical or spherical-like particles consist of drug dissolved and (or) dispersed homogeneously throughout a polymer material, with a particle size ranging in 1-500 μm, and generally prepared as suspensions for injection.

A lactide-glycolide copolymer is also referred to as poly (lactide-co-glycolide), abbreviated as PLGA. As used herein, the term "uncapped poly(lactide-co-glycolide)" refers to poly(lactide-co-glycolide) having a carboxyl terminal group, below abbreviated as PLGA.

The two copolymers, i.e., the two PLGAs, are an uncapped PLGA with a high intrinsic viscosity of 0.4-0.9 dl/g, preferably, 0.45-0.8 dl/g, more preferably, 0.45-0.55 dl/g, and an uncapped PLGA with a low intrinsic viscosity of 0.1-0.35 dl/g, preferably, 0.1-0.3 dl/g, more preferably, 0.2-0.3 dl/g. A weight ratio of the uncapped PLGA with the high intrinsic viscosity to the uncapped PLGA with the low intrinsic viscosity is (50-95):(5-50), preferably, (70-90):(10-30), more preferably, 80:20. A molar ratio of lactide to glycolide in the uncapped PLGA with the high intrinsic viscosity is within a range from 65:35 to 90:10, preferably, 75:25; and a molar ratio of lactide to glycolide in the uncapped PLGA with the low intrinsic viscosity is within a range from 50:50 to 75:25, preferably, 50:50.

The intrinsic viscosity of PLGA is determined by preparing an about 0.5% (w/v) solution of PLGA in chloroform, and determining the intrinsic viscosity of PLGA at 30° C. using a Cannon-Fenske glass capillary viscometer.

The two PLGAs may also be a high molecular weight PLGA with a molecular weight of 50,000-145,000, preferably, 55,000-110,000, more preferably, 55,000-85,000 and a low molecular weight PLGA with a molecular weight of 4,000 to 45,000, preferably, 4,000-35,000, more preferably, 15,000-35,000. A weight ratio of the high molecular weight PLGA to the low molecular weight PLGA is (50-95):(5-50), preferably, (70-90):(10-30), more preferably, 80:20. A molar ratio of lactide to glycolide in the high molecular weight PLGA is within a range from 65:35 to 90:10, preferably, 75:25; and a molar ratio of lactide to glycolide in the low molecular weight PLGA is within a range from 50:50 to 75:25, preferably, 50:50. As used herein, the term "molecular weight" refers to "weight average molecular weight", abbreviated as "molecular weight".

For convenient description, hereinafter, the molar ratio of lactide to glycolide in PLGA and the intrinsic viscosity of PLGA are expressed in a bracket after PLGA. For example, "PLGA (75/25, 0.5 A)" refers to a lactide-glycolide copolymer having an intrinsic viscosity of 0.5 dl/g and a carboxyl terminal group, in which a molar ratio of lactide to glycolide is 75:25.

Particularly, the preferred weight ratio of the uncapped PLGA (75/25, 0.5 A) with the high intrinsic viscosity to the uncapped PLGA (50/50, 0.25 A) with the low intrinsic viscosity in the present invention is 80:20.

Specifically, in the microsphere composition of the present invention, the preferred weight content of risperidone is 45% and the weight content of uncapped PLGA is 55%, the weight ratio of the two PLGAs is 80:20, the molecular weight of the two PLGAs are 55,000~85,000 and 15,000~35,000, the intrinsic viscosity of the two PLGAs are 0.45~0.55 dL/g and 0.2~0.3 dL/g, and molar ratio of lactide to glycolide in the two PLGAs are 75:25 and 50:50, respectively.

As used herein, a drug-loading rate refers to a practical drug-loading rate, which is calculated by a formula: drug-loading rate=[amount of drug in microspheres/(amount of drug in microspheres+amount of polymer in microspheres)]×100%.

Risperidone or 9-hydroxy risperidone in the sustained release microspheres of the present invention may be present in the form of a salt. An acid which will form a salt with risperidone or 9-hydroxy risperidone comprises an inorganic acid, for example, halogen acid (e.g., hydrochloric acid or hydrobromic acid), nitric acid, sulfuric acid or phosphoric acid; or an organic acid, for example, acetic acid, propionic acid, hydroxy acetic acid, 2-hydroxy propionic acid, pamoic acid, 2-oxo propionic acid, oxalic acid, malonic acid, succinic acid, 2-butenedioic acid, methanesulfonic acid, ethanesulfonic acid, benzenesulfonic acid or toluenesulfonic acid.

The risperidone sustained release microspheres of the present invention may be prepared by a conventional method, for example, an emulsion-solvent evaporation method, a spray drying method or a spray extraction method, etc.

Emulsion-Solvent Evaporation Method

Risperidone or a salt thereof or 9-hydroxy risperidone or a salt thereof and PLGA are dissolved in a suitable organic solvent, the organic solvent is injected into an aqueous solution prepared from a water soluble polymer to perform dispersion emulsifying, the organic solvent is evaporated, and the residue is washed and filtered to obtain microspheres. The organic solvent may be selected from halogenated hydrocarbons (e.g., dichloromethane, chloroform, ethyl chloride, dichloromethane, or trichloroethane), ethyl acetate, ethyl formate, diethyl ether, cyclohexane, benzyl alcohol, or a combination thereof. The water soluble polymer may be selected from at least one of polyvinyl alcohol (PVA), sodium carboxymethyl cellulose (CMC-Na), polyvinyl pyrrolidone (PVP), sodium polymethacrylate and sodium polyacrylate, or a combination of two or more of them. The dispersion emulsifying may be performed by mechanical stirring or by a static mixer.

Spray Drying Method

Risperidone or a salt thereof or 9-hydroxy risperidone or a salt thereof and PLGA are dissolved in a suitable organic solvent and filtered, and a conventional spray drying method is used to prepare microspheres. The organic solvent may be selected from dichloromethane, chloroform, ethyl acetate, diethyl ether, acetone, benzyl alcohol, glacial acetic acid, or a combination thereof.

Spray Extraction Method

Risperidone or a salt thereof or 9-hydroxy risperidone or a salt thereof and PLGA are dissolved in a suitable organic solvent to form a solution, and then the solution is sprayed into an organic nonsolvent (i.e., an organic solvent in which risperidone or a salt thereof or 9-hydroxy risperidone or a salt thereof and PLGA are not dissolved) or water, and extracted the solvent to form the microspheres. The organic solvent may be selected from dichloromethane, chloroform, ethyl acetate, diethyl ether, acetone, benzyl alcohol, glacial acetic acid, or a combination thereof. The organic nonsolvent may be selected from methanol, ethanol, propanol, isopropanol, petroleum ether, alkane, paraffine, or a combination thereof.

The present disclosure further provides a use of the risperidone microspheres in preparation of antipsychotic drugs, in which a psychosis comprises acute schizophrenia and chronic schizophrenia, significant positive symptoms (e.g., hallucination, delusion, thought disorder, hostility, or suspicion) and significant negative symptoms (e.g., slow response, emotional indifference, social indifference, or hypologia) of other psychotic states, and affective symptoms (e.g., depression, guilty feeling, or anxiety) related to schizophrenia, preferably, schizophrenia, anxiety, depression, periodic headache, etc.

In another embodiment, the present disclosure provides a method of treating psychosis by administering a formulation of risperidone microspheres described herein. The psychosis comprises acute schizophrenia and chronic schizophrenia, significant positive symptoms (e.g., hallucination, delusion, thought disorder, hostility, or suspicion) and significant negative symptoms (e.g., slow response, emotional indifference, social indifference, or hypologia) of other psychotic states, and affective symptoms (e.g., depression, guilty feeling, or anxiety) related to schizophrenia, preferably, schizophrenia, anxiety, depression, periodic headache, etc.

The microspheres according to an embodiment of the present disclosure may be present in the form of a sterile powder. The sterile powder may contain the risperidone microsphere composition and mannitol and may be prepared by washing the sustained release composition with water for injection, transferring the sustained release composition to a lyophilized plate, adding mannitol and an appropriate amount of injection water, placing the lyophilized plate in a lyophilizer for lyophilizing, subjecting the lyophilized product to screening and mixing, sterile subpackaging, and capping to obtain the sterile powder. Before administrating the drug to a patient, the sterile powder is suspended in an acceptable dispersion solvent. The dispersion solvent is selected from at least one of a suspending agent, a pH regulator, an isoosmotic adjusting agent, a surfactant, and water for injection. The suspending agent may be selected from at least one of sodium carboxymethyl cellulose, polyvinyl alcohol, polyvinyl pyrrolidone, sodium alginate, and glycerol. The isoosmotic adjusting agent may be selected from at least one of sodium chloride, glucose, mannitol, and glucitol. The surfactant is a nonionic surfactant, for example, polysorbate series (e.g., polysorbate 80 or polysorbate 60) or poloxamer series (e.g., poloxamer 188).

The risperidone sustained release microsphere composition according to an embodiment of the present disclosure is usually administrated parenterally, for example, intramuscular injection, subcutaneous injection, intradermal injection, intraperitoneal injection and so on. For a patient with a body weight of 60 kg, an administration dose is 12.5-150 mg every time, based on risperidone. That is, a therapeutically effective amount of the risperidone sustained release microsphere composition is 0.2-2.5 mg risperidone/kg body weight, preferably, 0.4-1.7 mg risperidone/kg body weight.

The sustained release microsphere composition has the following advantages: 1) it provides immediate release after entering into a body without drug release lag phase, in both high or low drug-loading; 2) it is conducive to scaled-up production (scale above 75 L) and without drug crystals precipitating out during the production; 3) it is highly stable, and therefore in vivo release behavior will not change after long-term storage.

BRIEF DESCRIPTION OF THE DRAWINGS

FIG. 1-1 is a scanning electron microscope image of risperidone microspheres in CN101653422, in which drug crystals are precipitated out.

FIG. 1-2 is a scanning electron microscope image of risperidone microspheres in Embodiment 6, in which no drug crystals are precipitated out, which indicates that the risperidone microspheres according to an embodiment of the present disclosure is suitable for large-scale industrialized production.

FIG. 2 shows in vivo release blood drug concentration-time curves of a risperidone microsphere composition (prepared according to CN101653422) before and after being stored for 6 months, which indicates that the in vivo drug release behavior of the risperidone microspheres in CN101653422 after being stored for 6 months changes substantially and the quality of the risperidone microspheres disclosed in CN101653422 is not stable.

FIG. 3 shows in vivo release blood drug concentration-time curves of risperidone microspheres in Embodiment 1 before and after being stored for 6 months, which indicates that in vivo drug release behavior of the risperidone microspheres in Embodiment 1 after being stored for 6 months does not change substantially and the quality of the risperidone microspheres according to an embodiment of the present disclosure is much more stable.

DETAILED DESCRIPTION

Figure 4:
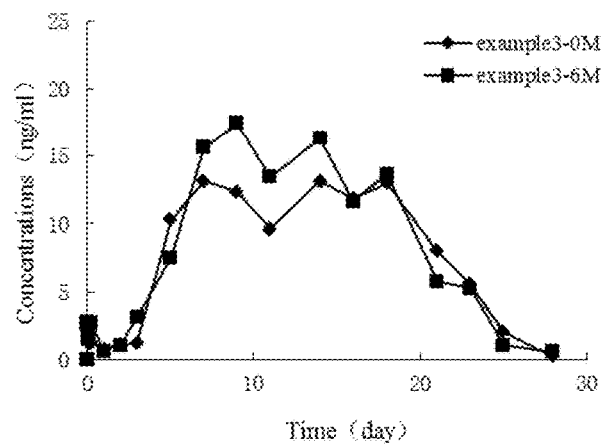
FIG. 4 shows in vivo release blood drug concentration-time curves of risperidone microspheres in Embodiment 3 before and after being stored for 6 months, which indicates that in vivo drug release behavior of the risperidone microspheres in Embodiment 3 after being stored for 6 months does not change substantially and the quality of the risperidone microspheres according to an embodiment of the present disclosure is much more stable.
Figure 5:
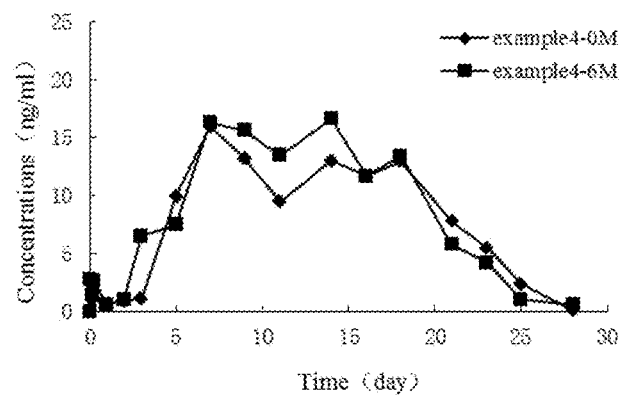
FIG. 5 shows in vivo release blood drug concentration-time curves of risperidone microspheres in Embodiment 4 before and after being stored for 6 months, which indicates that in vivo drug release behavior of the risperidone microspheres in Embodiment 4 after being stored for 6 months does not change substantially and the quality of the risperidone microspheres according to an embodiment of the present disclosure is much more stable.
Figure 6:
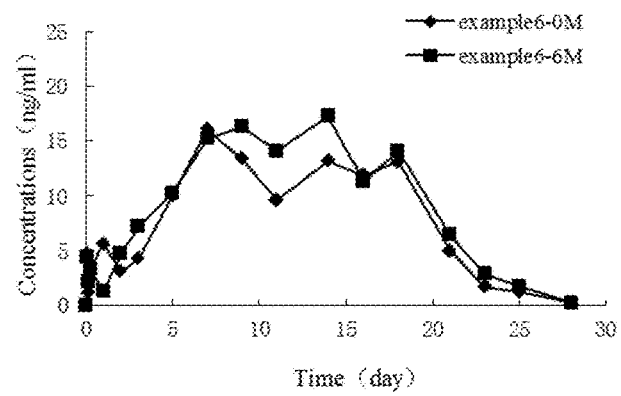
FIG. 6 shows in vivo release blood drug concentration-time curves of risperidone microspheres in Embodiment 6 before and after being stored for 6 months, which indicates that in vivo drug release behavior of the risperidone microspheres in Embodiment 6 after being stored for 6 months does not change substantially and the quality of the risperidone microspheres according to an embodiment of the present disclosure is much more stable.
Figure 7:
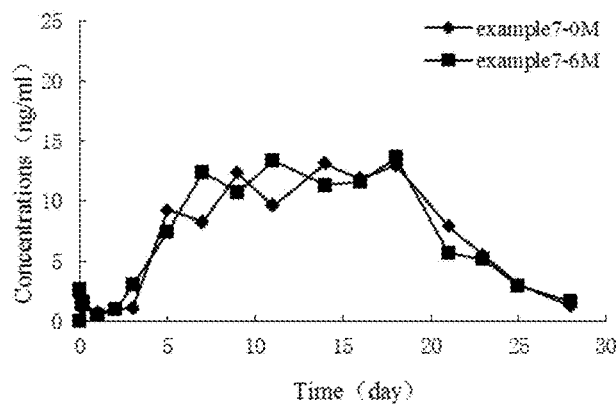
FIG. 7 shows in vivo release blood drug concentration-time curves of risperidone microspheres in Embodiment 7 before and after being stored for 6 months, which indicates that in vivo drug release behavior of the risperidone microspheres in Embodiment 7 after being stored for 6 months does not change substantially and the quality of the risperidone microspheres according to an embodiment of the present disclosure is much more stable.
Figure 8:
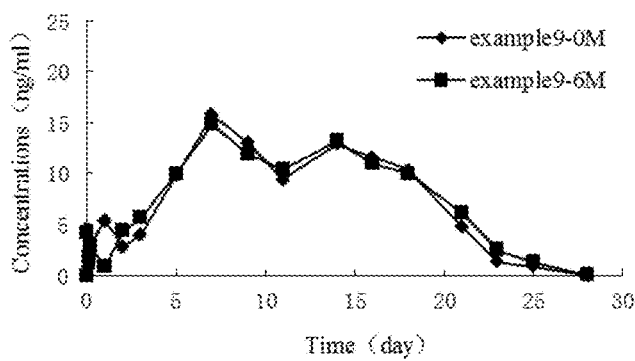
FIG. 8 shows in vivo release blood drug concentration-time curves of risperidone microspheres in Embodiment 9 before and after being stored for 6 months, which indicates that in vivo drug release behavior of the risperidone microspheres in Embodiment 9 after being stored for 6 months does not change substantially and the quality of the risperidone microspheres according to an embodiment of the present disclosure is much more stable.

As described herein, various embodiments are directed to pharmaceutical compositions, which comprise: an active component selected from risperidone, a salt thereof, 9-hydroxy risperidone and a salt thereof; and a polymer blend comprising a first uncapped poly(lactide-co-glycolide) and a second uncapped poly(lactide-co-glycolide), wherein a weight content of the active component in the pharmaceutical composition is within a range from 10% to 60%, preferably from 35% to 55%, more preferably from 40% to 50%; a weight content of the polymer blend in the pharmaceutical composition is within a range from 40% to 90%, preferably from 45% to 65%, more preferably from 50% to 60%; and the pharmaceutical composition is present in the form of microspheres.

In the pharmaceutical composition of one embodiment of the present disclosure, the polymer blend consists of the first uncapped poly(lactide-co-glycolide) and the second uncapped poly(lactide-co-glycolide).

In the pharmaceutical composition of one embodiment of the present disclosure, the first uncapped poly(lactide-co-glycolide) has a high intrinsic viscosity of 0.4-0.9 dl/g, preferably 0.45-0.8 dl/g, more preferably 0.45-0.55 dl/g, and the second uncapped poly(lactide-co-glycolide) has a low intrinsic viscosity of 0.1-0.35 dl/g, preferably 0.1-0.3 dl/g, more preferably 0.2-0.3 dl/g; and a weight ratio of the first uncapped poly(lactide-co-glycolide) to the second uncapped poly(lactide-co-glycolide) is (50-95):(5-50), preferably (70-90):(10-30), more preferably 80:20; and a molar ratio of lactide to glycolide in the first uncapped poly(lactide-co-glycolide) is within a range from 65:35 to 90:10, preferably 75:25; and a molar ratio of lactide to glycolide in the second uncapped poly(lactide-co-glycolide) is within a range from 50:50 to 75:25, preferably 50:50.

In the pharmaceutical composition of another embodiment of the present disclosure, the first uncapped poly(lactide-co-glycolide) has a weight average molecular weight of 50,000-145,000, preferably 55,000-110,000, more preferably 55,000-85,000 and the second uncapped poly(lactide-co-glycolide) has a weight average molecular weight of 4,000 to 45,000, preferably 4,000-35,000, more preferably 15,000-35,000; and a weight ratio of the first uncapped poly(lactide-co-glycolide) to the second uncapped poly(lactide-co-glycolide) is (50-95):(5-50), preferably (70-90):(10-30), more preferably 80:20; and a molar ratio of lactide to glycolide in the first uncapped poly(lactide-co-glycolide) is within a range from 65:35 to 90:10, preferably 75:25; and a molar ratio of lactide to glycolide in the second uncapped poly(lactide-co-glycolide) is within a range from 50:50 to 75:25, preferably 50:50.

In the pharmaceutical composition of one preferred embodiment of the present disclosure, the weight content of risperidone is 45%, the weight content of the polymer blend is 55%, the weight ratio of the first uncapped PLGA to the second uncapped PLGA is 80:20, the molecular weight of the first uncapped PLGA is 55,000~85,000 and the molecular weight of the second uncapped PLGA is 15,000~35,000, the intrinsic viscosity of the first uncapped PLGA is 0.45~0.55 dL/g and the intrinsic viscosity of the second uncapped PLGA is 0.2~0.3 dL/g, and a molar ratio of lactide to glycolide in the first uncapped PLGA is 75:25 and a molar ratio of lactide to glycolide in the second uncapped PLGA is 50:50.

In the pharmaceutical composition of one embodiment of the present disclosure, a salt of risperidone or 9-hydroxy risperidone is selected from an inorganic acid salt and an organic acid salt; the inorganic acid salt being selected from hydrochlorate, hydrobromate, nitrate, sulfate and phosphate; and the organic acid salt being selected from acetate, propionate, hydroxy acetate, 2-hydroxy propionate, pamoate, 2-oxo propionate, oxalate, malonate, succinate, 2-butenedioate, methanesulfonate, ethanesulfonate, benzenesulfonate and toluenesulfonate.

The present disclosure further provides a use of any one of the above-mentioned pharmaceutical compositions in preparation of antipsychotics, wherein a psychosis comprises acute schizophrenia and chronic schizophrenia, significant positive symptoms and significant negative symptoms of other psychotic states, and affective symptoms related to schizophrenia.

Another embodiment of the present disclosure provides a sustained release microsphere formulation for injection, comprising any one of the above-mentioned pharmaceutical compositions; and the microspheres are suspended in a pharmaceutically acceptable dispersion solvent; the dispersion solvent is selected from a suspending agent, a pH regulator, an isoosmotic adjusting agent, a surfactant, water, and physiological saline; and wherein the suspending agent is selected from sodium carboxymethyl cellulose, polyvinyl alcohol, polyvinyl pyrrolidone, sodium alginate, and glycerol; and wherein the isoosmotic adjusting agent is selected from sodium chloride, glucose, mannitol, and glucitol; and wherein the surfactant is a nonionic surfactant and is selected from polysorbate series and poloxamer series.

The present disclosure will be further illustrated by the following embodiments and test embodiments, which will not limit the scope of the present invention in any way.

Embodiment 1

72 g of PLGA (75/25, 0.52 A) with a molecular weight of 74,000, 18 g of PLGA (50/50, 0.25 A) with a molecular weight of 25,000 and 110 g of risperidone were weighed and dissolved in 1000 ml of dichloromethane with stirring to prepare a clear solution. The clear solution was added into a microsphere preparation kettle containing a 100 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 45.9% and an encapsulation efficiency of 83.5%.

Embodiment 2

67.5 g of PLGA (75/25, 0.42 A) with a molecular weight of 55,000, 7.5 g of PLGA (50/50, 0.25 A) with a molecular weight of 25,000 and 75 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 40.2% and an encapsulation efficiency of 80.4%.

Embodiment 3

56 g of PLGA (75/25, 0.90 A) with a molecular weight of 125,000, 24 g of PLGA (50/50, 0.25 A) with a molecular weight of 25,000 and 120 g of risperidone were weighed and dissolved in 1000 ml of dichloromethane with stirring to prepare a clear solution. The clear solution was added into a microsphere preparation kettle containing a 100 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 51.5% and an encapsulation efficiency of 85.8%.

Embodiment 4

64.125 g of PLGA (75/25, 0.52 A) with a molecular weight of 74,000, 3.375 g of PLGA (50/50, 0.10 A) with a molecular weight of 4,200 and 82.5 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 45.5% and an encapsulation efficiency of 82.7%.

Embodiment 5

63 g of PLGA (75/25, 0.52 A) with a molecular weight of 74,000, 27 g of PLGA (50/50, 0.35 A) with a molecular weight of 40,000 and 60 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 33.1% and an encapsulation efficiency of 82.8%.

Embodiment 6

42 g of PLGA (65/35, 0.55 A) with a molecular weight of 85,000, 10.5 g of PLGA (50/50, 0.25 A) with a molecular weight of 25,000 and 97.5 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 55.0% and an encapsulation efficiency of 84.6%.

Embodiment 7

57.75 g of PLGA (90/10, 0.45 A) with a molecular weight of 67,000, 24.75 g of PLGA (50/50, 0.25 A) with a molecular weight of 25,000 and 67.5 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 35.8% and an encapsulation efficiency of 79.6%.

Embodiment 8

68.25 g of PLGA (85/15, 0.71 A) with a molecular weight of 110,000, 36.75 g of PLGA (50/50, 0.25 A) with a molecular weight of 25,000 and 45 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 23.9% and an encapsulation efficiency of 79.7%.

Embodiment 9

54 g of PLGA (75/25, 0.52 A) with a molecular weight of 74,000, 13.5 g of PLGA (75/25, 0.20 A) with a molecular weight of 25,000 and 82.5 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 45.3% and an encapsulation efficiency of 82.4%.

Embodiment 10

60 g of PLGA (85/15, 0.71 A) with a molecular weight of 110,000, 60 g of PLGA (50/50, 0.25 A) with a molecular weight of 25,000 and 30 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 13.9% and an encapsulation efficiency of 69.5%.

Embodiment 11

48 g of PLGA (75/25, 0.61 A) with a molecular weight of 92,000, 12 g of PLGA (65/35, 0.12 A) with a molecular weight of 5,000 and 140 g of risperidone were weighed and dissolved in 1000 ml of dichloromethane with stirring to prepare a clear solution. The clear solution was added into a microsphere preparation kettle containing a 100 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 60.6% and an encapsulation efficiency of 84.3%.

Embodiment 12

54 g of PLGA (75/25, 0.52 A) with a molecular weight of 74,000, 13.5 g of PLGA (50/50, 0.25 A) with a molecular weight of 25,000 and 85.65 g of 9-hydroxy risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 45.9% and an encapsulation efficiency of 83.5%.

Embodiment 13

64.8 g of PLGA (75/25, 0.52 A) with a molecular weight of 74,000, 16.2 g of PLGA (50/50, 0.25 A) with a molecular weight of 25,000 and 192.6 g of pamoic acid risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. No crystals were precipitated out. The microspheres had a drug-loading rate of 45.9% and an encapsulation efficiency of 83.5%.

Embodiment 14

The microspheres obtained in Embodiment 1 were washed with water for injection and transferred to a lyophilized plate. 4 g of mannitol and an appropriate amount of water were added, and the lyophilized plate was placed in a lyophilizer for lyophilizing. The lyophilized product was subjected to screening and mixing, sterile subpackaging, and capping to obtain risperidone sustained release microspheres for injection.

Comparative Test 1 Scaled-up Production Of Risperidone Microspheres Disclosed In CN101653422 (75 L)

1) Test Materials Risperidone, PLGA (75/25, 0.52 A) with a molecular weight of 74,000

2) Method and Results:

60 g of PLGA (75/25, 0.52 A) with a molecular weight of 74,000 and 90 g of risperidone were weighed and dissolved in 750 ml of dichloromethane with stirring to prepare a clear solution. The clear solution was added into a microsphere preparation kettle containing a 75 L PVA solution (0.5%) cooled to 6° C. by a peristaltic pump. A stirrer and a homogenizer were started, and then the clear solution was homogeneously emulsified at 380 rpm for 1 min. Then, the rotation speed of the homogenizer was reduced, and an organic solvent was evaporated for 3-5 h. The residue was filtered with a screen, washed with deionized water, and lyophilized to obtain powdered microspheres. After observed by a microscope, drug crystals were discovered, as shown in FIG. 1-1.

In contrast, the microspheres obtained in Embodiments 1-10 according to the present disclosure, when observed by a microscope, showed no drug crystals that precipitated out. FIG. 1-2 is a scanning electron microscope image of risperidone microspheres in Embodiment 6.

The results indicate that the risperidone microspheres according to an embodiment of the present disclosure are more suitable for large-scale industrialized production.

Comparative Test 2 Stability Test Of An Embodiment of The Present Disclosure As Compared With CN101653422

1) Test Materials

Test Drugs:

The present disclosure: the risperidone microspheres obtained in Embodiments 1, 3, 4, 6, 7, 9 were stored for 0 month and 6 months respectively.

CN101653422: the risperidone microspheres obtained in Embodiment 3 in CN101653422 was stored for 0 month and 6 months. 4.0 g of PLGA (75/25, 0.52 A) with a molecular weight of 74,000 and 6.0 g of risperidone were weighed and dissolved in 50 ml of dichloromethane with stirring to prepare a clear solution. The clear solution was added into a microsphere preparation kettle containing a 5000 ml PVA solution (0.5%) cooled to 6° C. with high-speed stirring by a peristaltic pump, and dispersion emulsified at 1000 rpm for 1 min. Then, the rotation speed was adjusted to 300 rpm, the rotation speed of a stirring paddle was 150 rpm, and any organic solvent was removed by evaporation for 6 h. The residue was filtered with a screen, washed with deionized water 5 times, and lyophilized to obtain powdered microspheres. The microspheres had a drug-loading rate of 50.7% and an encapsulation efficiency of 84.5%.

Test Animals: 56 healthy beagles dogs, 4 dogs in each group, 28-female-28-male, with a body weight of 9.5-10.5 kg.

Test Instruments: an API 4000 triple quadrupole tandem mass spectrometer equipped with an ion spray ionization source and an Analyst 1.4 data processing software, U.S., Applied Biosystem company; Agilent 1100 high performance liquid chromatograph.

2) Method and Results

The test animals were randomly divided into 2 groups (0-month group and 6-month group) with 4 dogs in each group, a dose of 1.5 mg/kg (based on risperidone) was administrated by intramuscular injection on each beagle, and after administrating for 0 h, 1 h, 3 h, 6 h, 1 d, 2 d, 3 d, 5 d, 7 d, 9 d, 11 d, 14 d, 16 d, 18 d, 21 d, 23 d, 25 d, and 28 d, 3 ml of blood was sampled via the forelimb vein of each beagle, placed in the heparinization centrifuge tube immediately, and centrifugated for 10 min (3600 rpm). A plasma was separated, and stored in a refrigerator at −37° C. to be measured. Drug blood concentrations of risperidone and a metabolite thereof, i.e., 9-hydroxy risperidone, in the plasma were measured respectively, and the results were shown in Table 1 and FIGS. 2-8.

It may be seen from the results that there was substantial changes in the in vivo drug release behavior of the risperidone microspheres disclosed in CN101653422 after being stored for 6 months; but the in vivo drug release behavior of the risperidone microspheres according to an embodiment of the present disclosure after being stored for 6 months does not change substantially due to improved stability.

TABLE 1

Drug blood concentrations (ng/mL) at different time after the microspheres according to an embodiment of the present disclosure and in CN101653422 after stored for 6 months were administrated by intramuscular injection on each beagle

| Time | Embodiment 1 | | Embodiment 3 | | Embodiment 4 | | Embodiment 6 | |
|---|---|---|---|---|---|---|---|---|
| (day) | 0 month | 6 month | 0 month | 6 month | 0 month | 6 month | 0 month | 6 month |
| 0 | 0 | 0 | 0 | 0 | 0 | 0 | 0 | 0 |
| 0.042 | 2.619 | 2.593 | 2.126 | 2.739 | 2.635 | 2.817 | 4.792 | 4.469 |
| 0.125 | 1.665 | 2.326 | 1.156 | 1.512 | 1.049 | 1.55 | 1.186 | 2.202 |
| 0.25 | 1.79 | 3.449 | 1.209 | 2.665 | 1.174 | 2.673 | 3.311 | 3.325 |
| 1 | 1.268 | 1.406 | 0.786 | 0.607 | 0.652 | 0.630 | 5.662 | 1.282 |
| 2 | 1.589 | 1.860 | 1.096 | 1.058 | 0.973 | 1.084 | 3.110 | 4.739 |
| 3 | 1.73 | 3.928 | 1.205 | 3.122 | 1.114 | 6.569 | 4.265 | 7.221 |
| 5 | 10.561 | 8.32 | 10.262 | 7.536 | 9.945 | 7.544 | 10.082 | 10.298 |
| 7 | 16.548 | 19.789 | 13.099 | 15.621 | 15.932 | 16.336 | 16.069 | 15.223 |
| 9 | 12.837 | 18.237 | 12.337 | 17.433 | 13.229 | 15.623 | 13.366 | 16.275 |
| 11 | 10.125 | 14.214 | 9.625 | 13.414 | 9.509 | 13.438 | 9.646 | 14.09 |
| 14 | 13.641 | 17.38 | 13.114 | 16.33 | 13.025 | 16.604 | 13.162 | 17.256 |
| 16 | 12.326 | 12.427 | 11.865 | 11.627 | 11.71 | 11.651 | 11.847 | 11.301 |
| 18 | 13.582 | 14.195 | 13.006 | 13.656 | 12.966 | 13.419 | 13.103 | 14.071 |
| 21 | 8.48 | 6.581 | 7.980 | 5.781 | 7.864 | 5.805 | 5.007 | 6.457 |
| 23 | 6.155 | 5.027 | 5.565 | 5.227 | 5.539 | 4.251 | 1.676 | 2.903 |
| 25 | 3.004 | 1.866 | 2.069 | 1.066 | 2.388 | 1.090 | 1.230 | 1.742 |
| 28 | 0.713 | 1.386 | 0.231 | 0.583 | 0.097 | 0.610 | 0.234 | 0.213 |

| Time | Embodiment 7 | | Embodiment 9 | | CN101653422 | |
|---|---|---|---|---|---|---|
| (day) | 0 month | 6 month | 0 month | 6 month | 0 month | 6 month |
| 0 | 0 | 0 | 0 | 0 | 0 | 0 |
| 0.042 | 2.098 | 2.661 | 4.496 | 4.112 | 2.919 | 2.369 |
| 0.125 | 1.097 | 1.434 | 0.89 | 1.845 | 2.014 | 1.628 |
| 0.25 | 1.15 | 1.562 | 3.015 | 2.968 | 2.795 | 1.76 |
| 1 | 0.727 | 0.529 | 5.366 | 0.925 | 1.213 | 1.138 |
| 2 | 1.037 | 0.98 | 2.814 | 4.382 | 1.497 | 0.804 |
| 3 | 1.146 | 3.044 | 3.969 | 5.621 | 1.8595 | 0.62 |
| 5 | 9.203 | 7.458 | 9.786 | 9.941 | 7.2195 | 5.335 |
| 7 | 8.268 | 12.361 | 15.773 | 14.866 | 15.9145 | 5.314 |
| 9 | 12.278 | 10.695 | 13.07 | 11.902 | 14.361 | 8.079 |
| 11 | 9.566 | 13.336 | 9.35 | 10.356 | 12.0665 | 7.719 |
| 14 | 13.055 | 11.252 | 12.866 | 13.231 | 16.868 | 13.095 |
| 16 | 11.806 | 11.549 | 11.551 | 10.944 | 11.955 | 17.679 |

TABLE 1-continued

Drug blood concentrations (ng/mL) at different time after the microspheres according to an embodiment of the present disclosure and in CN101653422 after stored for 6 months were administrated by intramuscular injection on each beagle

| | | | | | | |
|---|---|---|---|---|---|---|
| 18 | 12.947 | 13.578 | 10.32  | 9.967 | 12.998 | 20.781 |
| 21 | 7.921  | 5.703  | 4.711  | 6.1   | 6.044  | 18.068 |
| 23 | 5.506  | 5.149  | 1.38   | 2.546 | 3.026  | 9.215  |
| 25 | 3.056  | 2.988  | 0.934  | 1.385 | 1.727  | 4.123  |
| 28 | 1.265  | 1.658  | 0.063  | 0.123 | 1.3495 | 2.136  |

Comparative Test 3 Release Results Of Risperidone Microspheres Of The Present Disclosure With Different Drug-Loading Rates In Dog Bodies Compared With Release Results Of Risperidone Microspheres In CN101653422 With Different Drug-Loading Rates In Dog Bodies 1) Test Materials Test Drugs:

The present disclosure: the risperidone microspheres with drug-loading rates of 13.9%, 23.9%, 33.1%, 40.2% obtained in Embodiments 2, 5, 8, 10 respectively.

CN101653422: the risperidone microspheres with drug-loading rates of 45.5%, 40.3%, 35.6% obtained according to Embodiments 7-9 of CN101653422, respectively.

Test Animals: 24 healthy beagles dogs, 4 dogs in each group, 12-female-12-male, with a body weight of 9.5-10.5 kg.

Test Instruments: the same as those in Test Embodiment 2.

2) Method and Results

The test method is the same as that in Test Embodiment 2.

Figure 9:
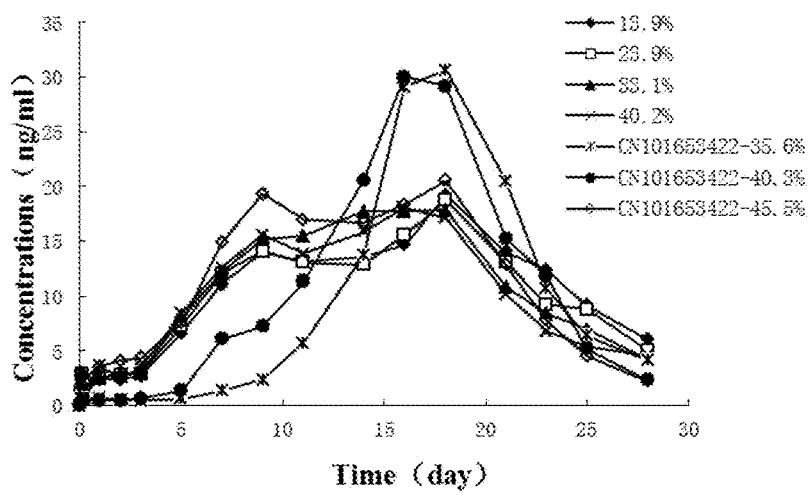
FIG. 9 shows in vivo release blood drug concentration-time curves of risperidone microspheres in Test embodiment 2, which indicates that a drug may be still released immediately after entering into a body even when the drug-loading rate of the risperidone microspheres according to an embodiment of the present disclosure as low as about 20%, without a release lag phase.

The test results were shown in Table 2 and FIG. 9.

The results show that, for the risperidone microspheres in CN101653422, the drug may not be released immediately after entering into a body when the drug-loading rate is below 45%, i.e., there is a release lag phase. In contrast, for the risperidone microspheres according to an embodiment of the present disclosure, the drug may still be released immediately after entering into a body even when the drug-loading rate of is as low as about 10%, i.e., there is not a release lag phase.

TABLE 2

Drug blood concentrations (ng/mL) at different times after the microspheres according to an embodiment of the present disclosure and in CN101653422 were administrated by intramuscular injection on each beagle

| Time | Drug-loading rate | | | | | | |
|---|---|---|---|---|---|---|---|
| | The present disclosure | | | | CN101653422 | | |
| (day) | 13.9% | 23.9% | 33.1% | 40.2% | 35.6% | 40.3% | 45.5% |
| 0     | 0      | 0      | 0      | 0      | 0      | 0      | 0      |
| 0.042 | 1.011  | 1.028  | 1.059  | 1.428  | 0.635  | 0.233  | 3.023  |
| 0.125 | 2.365  | 2.846  | 2.991  | 1.367  | 0.621  | 0.412  | 2.566  |
| 0.25  | 1.652  | 1.899  | 1.051  | 1.423  | 0.619  | 0.411  | 2.651  |
| 1     | 2.368  | 2.486  | 2.628  | 3.577  | 0.617  | 0.405  | 3.553  |
| 2     | 2.356  | 2.786  | 2.938  | 2.509  | 0.539  | 0.455  | 4.065  |
| 3     | 2.669  | 2.895  | 3.047  | 3.416  | 0.432  | 0.636  | 4.322  |
| 5     | 6.659  | 7.296  | 8.104  | 8.473  | 0.612  | 1.323  | 7.587  |
| 7     | 11.026 | 12.018 | 12.169 | 12.538 | 1.321  | 6.036  | 14.852 |
| 9     | 14.011 | 14.058 | 15.179 | 15.548 | 2.365  | 7.229  | 19.286 |
| 11    | 13.102 | 13.022 | 15.469 | 13.838 | 5.691  | 11.292 | 16.963 |
| 14    | 13.561 | 12.804 | 17.697 | 15.838 | 13.665 | 20.552 | 16.665 |
| 16    | 14.667 | 15.556 | 17.707 | 18.076 | 29.053 | 30.026 | 18.337 |
| 18    | 19.223 | 18.696 | 17.808 | 17.102 | 30.658 | 29.199 | 20.544 |
| 21    | 14.003 | 13.085 | 10.822 | 10.191 | 20.511 | 15.236 | 12.802 |
| 23    | 12.325 | 9.236  | 8.407  | 6.776  | 10.664 | 11.813 | 7.801  |
| 25    | 9.166  | 8.805  | 6.957  | 5.364  | 6.366  | 5.221  | 4.503  |
| 28    | 6.076  | 5.016  | 4.196  | 4.535  | 4.112  | 2.323  | 2.209  |

The invention claimed is:

1. A pharmaceutical composition comprising:
    a pharmaceutically active component selected from risperidone or a salt thereof, 9-hydroxy risperidone or a salt thereof; and
    a polymer blend comprising a first uncapped poly(lactide-co-glycolide) and a second uncapped poly(lactide-co-glycolide), wherein the polymer blend does not have a capped poly(lactide-co-glycolide),
    wherein the first uncapped poly(lactide-co-glycolide) has a molar ratio of lactide to glycolide of 65:35 to 90:10; and the second uncapped poly(lactide-co-glycolide) has a molar ratio of lactide to glycolide of 50:50 to 75:25; and
    wherein the pharmaceutical composition is in the form of microspheres.

2. The pharmaceutical composition according to claim 1, wherein the molar ratio of lactide to glycolide in the first uncapped poly(lactide-co-glycolide) is 75:25; and the molar ratio of lactide to glycolide in the second uncapped poly(lactide-co-glycolide) is 50:50.

3. The pharmaceutical composition according to claim 1, wherein the first uncapped poly(lactide-co-glycolide) has an intrinsic viscosity of 0.4-0.9 dl/g, and the second uncapped poly(lactide-co-glycolide) has an intrinsic viscosity of 0.1-0.35 dl/g.

4. The pharmaceutical composition according to claim 3 wherein the first uncapped poly(lactide-co-glycolide) has an intrinsic viscosity of 0.45-0.8 dl/g; and the second uncapped poly(lactide-co-glycolide) has an intrinsic viscosity of 0.1-0.3 dl/g.

5. The pharmaceutical composition according to claim 4 wherein the first uncapped poly(lactide-co-glycolide) has an intrinsic viscosity of 0.45-0.55 dl/g; and the second uncapped poly(lactide-co-glycolide) has an intrinsic viscosity of 0.2-0.3 dl/g.

6. The pharmaceutical composition according to claim 1, wherein the first uncapped poly(lactide-co-glycolide) has a weight average molecular weight of 50,000-145,000, and the second uncapped poly(lactide-co-glycolide) has a weight average molecular weight of 4,000-45,000.

7. The pharmaceutical composition according to claim 6 wherein the first uncapped poly(lactide-co-glycolide) has a weight average molecular weight of 55,000-110,000; and the second uncapped poly(lactide-co-glycolide) has a weight average molecular weight of 4,000-35,000.

8. The pharmaceutical composition according to claim 7 wherein the first uncapped poly(lactide-co-glycolide) has a weight average molecular weight of 55,000-85,000; and the second uncapped poly(lactide-co-glycolide) has a weight average molecular weight of 15,000-35,000.

9. The pharmaceutical composition according to claim 1, wherein the first uncapped poly(lactide-co-glycolide) is present in the polymer blend at 50-95 wt % and the second uncapped poly(lactide-co-glycolide) is present in the polymer blend at 5-50 wt %.

10. The pharmaceutical composition according to claim 9, wherein the first uncapped poly(lactide-co-glycolide) is present in the polymer blend at 70-90 wt % and the second uncapped poly(lactide-co-glycolide) is present in the polymer blend at 10-30 wt %.

11. The pharmaceutical composition according to claim 10, wherein the first uncapped poly(lactide-co-glycolide) is present in the polymer blend at 80 wt % and the second uncapped poly(lactide-co-glycolide) is present in the polymer blend at 20 wt %.

12. The pharmaceutical composition according to claim 1, wherein a weight content of the pharmaceutically active component in the microspheres is within a range from 10% to 60%; and a weight content of the polymer blend in the microspheres is within a range from 40% to 90%.

13. The pharmaceutical composition according to claim 12, wherein a weight content of the pharmaceutically active component in the microspheres is within a range of 35%-55%; and a weight content of the polymer blend in the microspheres is within a range of 45%-65%.

14. The pharmaceutical composition according to claim 13, wherein a weight content of the pharmaceutically active component in the microspheres is within a range of 40%-50%; and a weight content of the polymer blend in the microspheres is within a range of 50%-60%.

15. The pharmaceutical composition according to claim 1, wherein the weight content of risperidone is 45% of the microspheres, the weight content of the polymer blend is 55% of the microspheres, the weight ratio of the first uncapped PLGA to the second uncapped PLGA is 80:20, the molecular weight of the first uncapped PLGA is 55,000 to 85,000 and the molecular weight of the second uncapped PLGA is 15,000 to 35,000, the intrinsic viscosity of the first uncapped PLGA is 0.45 to 0.55 dL/g and the intrinsic viscosity of the second uncapped PLGA is 0.2 to 0.3 dL/g, and a molar ratio of lactide to glycolide in the first uncapped PLGA is 75:25 and a molar ratio of lactide to glycolide in the second uncapped PLGA is 50:50.

16. The pharmaceutical composition according to claim 1, wherein the salt of risperidone or 9-hydroxy risperidone is selected from an inorganic acid salt and an organic acid salt; the inorganic acid salt being selected from hydrochlorate, hydrobromate, nitrate, sulfate and phosphate; and the organic acid salt being selected from acetate, propionate, hydroxy acetate, 2-hydroxy propionate, pamoate, 2-oxo propionate, oxalate, malonate, succinate, 2-butenedioate, methanesulfonate, ethanesulfonate, benzenesulfonate and toluenesulfonate.

17. A sustained release injectable formulation comprising the pharmaceutical composition of claim 1 and a pharmaceutically acceptable excipient.

18. The sustained release injectable formulation of claim 17 wherein the pharmaceutically acceptable excipient is a suspending agent, a pH regulator, an isoosmotic adjusting agent, a surfactant, water, physiological saline or a combination thereof; and wherein the suspending agent is selected from sodium carboxymethyl cellulose, polyvinyl alcohol, polyvinyl pyrrolidone, sodium alginate, and glycerol; and wherein the isoosmotic adjusting agent is selected from sodium chloride, glucose, mannitol, and glucitol; and wherein the surfactant is a nonionic surfactant and is selected from polysorbate series and poloxamer series.

19. A method for treating psychosis in a subject in need of treatment, the method comprising administering to the subject a sustained release injectable formulation of claim 17, wherein the psychosis is acute schizophrenia, chronic schizophrenia, significant positive symptoms, significant negative symptoms of other psychotic states, and affective symptoms related to schizophrenia.

20. The method of claim 19 wherein the pharmaceutical composition releases the active component in a sustained manner for a period of up to 28 days.

* * * * *